United States Patent [19]

Muto

[11] 4,223,671
[45] Sep. 23, 1980

[54] ENDOTRACHEAL TUBE STABILIZER

[76] Inventor: Rudolph Muto, 24 Williams St., Andover, Mass. 01801

[21] Appl. No.: 23,652

[22] Filed: Mar. 26, 1979

[51] Int. Cl.³ .............................................. A61M 16/00
[52] U.S. Cl. ........................... 128/200.26; 128/207.17; 128/DIG. 26
[58] Field of Search ....................... 128/200.26, 207.14, 128/207.15, 207.16, 207.17, 348–350, DIG. 26, 12

[56] References Cited

U.S. PATENT DOCUMENTS

| 1,270,565 | 6/1918 | Teter | 128/207.16 X |
|---|---|---|---|
| 2,820,457 | 1/1958 | Phillips | 128/200.26 |
| 2,908,269 | 10/1959 | Cheng | 128/207.14 |
| 3,756,244 | 9/1973 | Kinnear et al. | 128/207.14 |
| 3,924,636 | 12/1975 | Addison | 128/207.14 X |
| 3,946,742 | 3/1976 | Eross | 128/207.17 |
| 4,166,467 | 9/1979 | Abramson | 128/207.14 |
| 4,167,946 | 9/1979 | Sandstrom | 128/207.17 |

FOREIGN PATENT DOCUMENTS 669840  1/1939  Fed. Rep. of Germany ...... 128/207.14

Primary Examiner—Dalton L. Truluck
Attorney, Agent, or Firm—Pearson & Pearson

[57] ABSTRACT

An endotracheal tube stabilizer avoids the pain of repeatedly stripping tape from the face of a patient, which affixes an endotracheal tube in position, and avoids damage caused by continuous pressure on one spot of a patient's mouth and teeth on a bite block by providing a faceplate held in position by strands around the head, a wide slot in the faceplate and a mouthpiece slidable to selected positions along the slot. Thus the tube may be adhesive taped to the mouthpiece but the mouthpiece and its taped tube may be slid sidewise in the slot when deemed necessary for the welfare and comfort of the patient.

11 Claims, 5 Drawing Figures

ENDOTRACHEAL TUBE STABILIZER

BACKGROUND OF THE INVENTION

Endotracheal tube holders, clamps or retainers have long been known and have usually consisted of a faceplate, tied by a strap around the back of the patient's head, and covering the mouth area of the patient, there being a single aperture in the faceplate for receiving the endotracheal tube. Such devices are disclosed in U.S. Pat. No. 2,820,457 to Phillips of Jan. 21, 1958 wherein the faceplate is a flange integral with the mouthpiece and bite block and in U.S. Pat. No. 2,908,269 to Cheng of Oct. 13, 1959 wherein the faceplate has a tubular integral bite block on the side and an open slot on the other side for the tube.

The prior art also reveals a line of clamp type faceplates for clamping on an endotracheal tube as disclosed in U.S. Pat. Nos. 3,602,227 of Aug. 31, 1971 and 3,760,811 of Sept. 25, 1973 to Andrew wherein the two sections of the clamp lock together around the tube but must be broken to remove the tube. A pivoted jaw type clamp is disclosed in U.S. Pat. No. 3,993,081 to Cussell of Nov. 23, 1976 wherein there may be two holes for two tubes but the device makes use of adhesive tape on the skin of the patient which applicant has found to be objectionable.

SUMMARY OF THE INVENTION

In this invention, an endotracheal tube stabilizer is provided which is not affixed to the skin of the patient, the removal thereof for shifting the position of the bite block, having been found to be extremely painful especially for a whiskered male adult. The stabilizer of the invention therefore comprises a relatively wide faceplate of soft flexible plastic material with one, or sometimes two, integral ears on each side by which it can be flexed to conform to the patient's face and tied by tapes, strands, etc. around the patient's head.

The faceplate includes a central, wide, closed-end slot, substantially equal in width to the width of the patient's mouth and the slot having spaced upper and lower edges generally in parallelism and equally spaced apart. Integral, oppositely disposed pairs of bendable prongs are provided along the edges of the slot to define a right side aperture, a central aperture and a left side aperture.

A mouthpiece, preferably of plastic is mounted for sidewise sliding movement in the slot, held in place by front and rear flanges and having an axial bore generally normal to the face plate, a tubular bite block portion and a tubular guide portion.

The portion of the tubular mouthpiece between the front and rear flanges is flat at top and bottom to slide in the slot but to prevent turning.

DESCRIPTION OF THE PREFERRED EMBODIMENT

Figure 1:
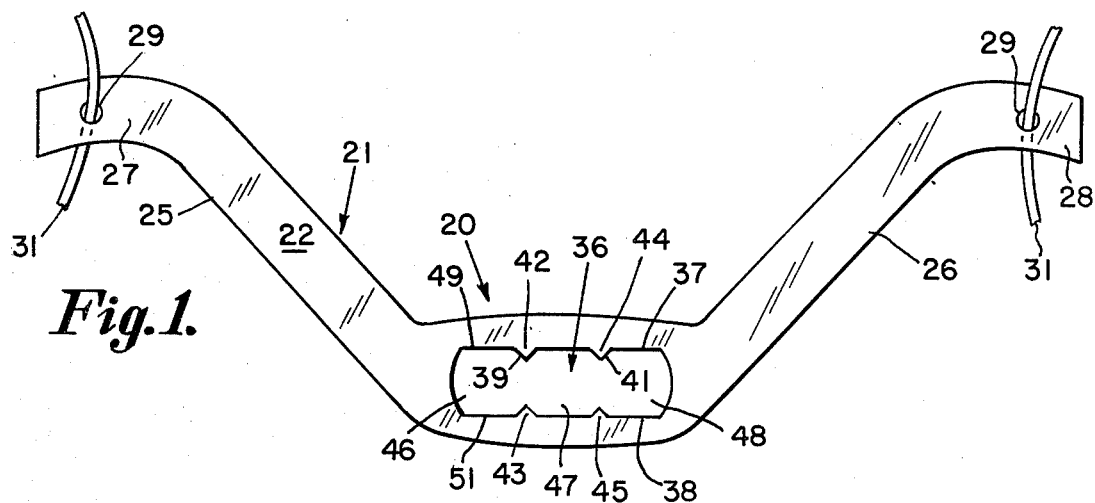
FIG. 1 is a front elevation of one embodiment of the flexible faceplate of the invention.
Figure 2:
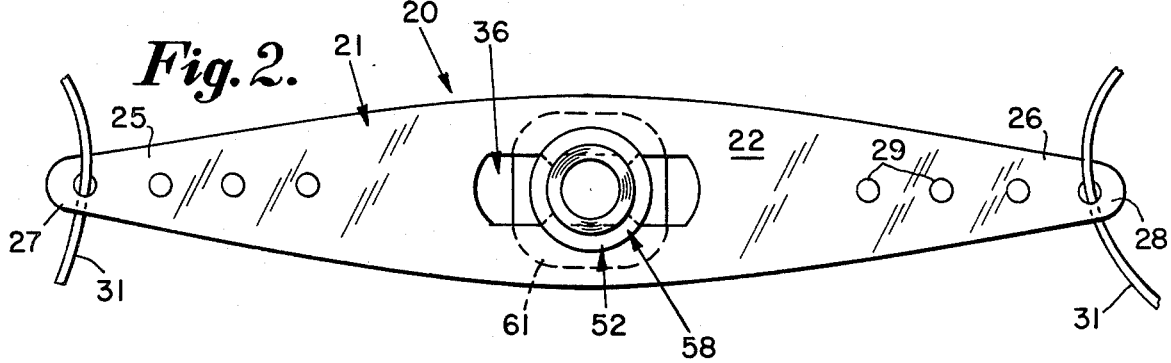
FIG. 2 is a view similar to FIG. 1 showing the tubular mouthpiece of the invention retained in the slot in another embodiment of the faceplate.
Figure 3:
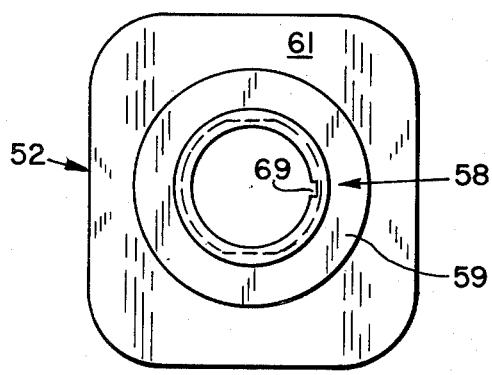
FIG. 3 is a front elevation of the mouthpiece.
Figure 4:
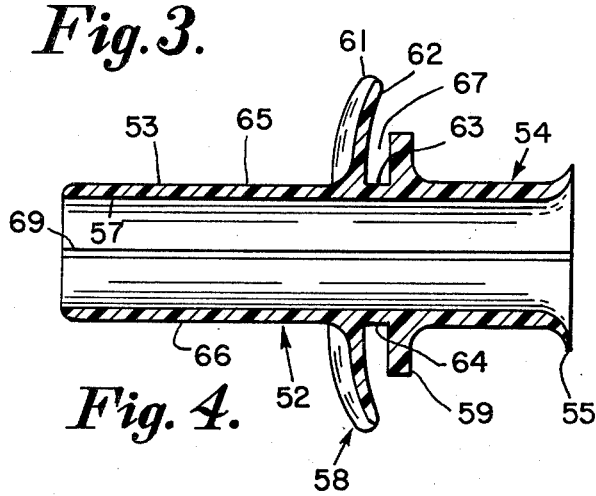
FIG. 4 is a side elevation in half section of the mouthpiece.
Figure 5:
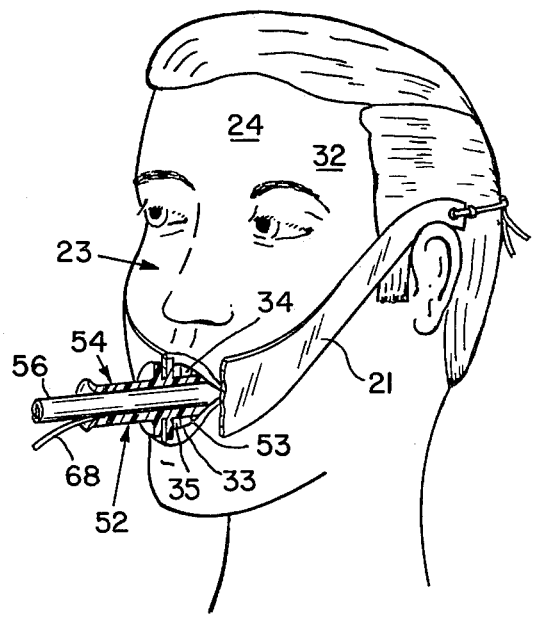
FIG. 5 is a perspective view of the device in use.

The endotracheal tube stabilizer 20, of the invention includes the faceplate, flange, or collar 21, which is preferably of soft, flexible, resilient plastic 22 so that it will easily conform to the configuration of the face 23 of a patient 24. Faceplate 21 includes at least one pair of integral ears 25 and 26 each of substantial length and terminating in tips 27 and 28, each having holes such as 29 for strands 31 of ribbon, tape or the like for tying around the head 32 of the patient 24 to position the faceplate over the mouth 33 of the patient. The faceplate 20 is of predetermined width at least equal to the width of the mouth 33 of a patient 24 and is of predetermined height at least sufficient to abut and cover the mouth 33, upper front teeth 34 and lower front teeth 35.

Face plate 21 is provided centrally with a wide slot 36 which is substantially coextensive in width with the width of the mouth 33 of a patient and which includes upper edge 37 and lower edge 38 which are equally spaced apart and in substantial parallelism except for two pairs 39 and 41 of oppositely disposed integral flexible, resilient prongs such as 42, 43, 44 and 45. The pairs 39 and 41 of prings divided the slot 36 into a left side aperture 46, a central aperture 47 and a right side apparatus 48, each with straight, or flat, upper and lower walls, or edges, as at 49 and 51 which are in parallelism.

The tubular mouthpiece 52 of the invention includes a tubular portion 53, forming a "bite block," which portion enters the mouth 33 of the patient 24 for receiving the bite of the upper front teeth 34 and the lower front teeth 35 and includes a tubular guide portion 54 extending away from the mouth 33 and flared at 55 for receiving and guiding an endotracheal tube 56. The mouthpiece 52 includes an axial bore 57 of uniform diameter which extends generally normal to faceplate 21 and which slidably receives the tube 56.

Flange means 58 is provided for retaining the mouthpiece 52 in slot 36 while permitting selective sidewise movement therein. Means 58 includes a front flange 59 of circular flat configuration spaced from a rear flange 61 of generally square configuration, flange 61 being concave curved in plan to conform to the curve of the teeth of the patient. The central portion 62 of rear flange 61 is spaced from the front flange 59 a distance substantially equal to the thickness of the material 22 of the faceplate so as to prevent forward or rearward tilting of the mouthpiece relative to the faceplate while enabling side wise sliding movement of the mouthpiece in the slot 36. The upper surface 63 and the lower surface 64 of the portion of mouthpiece 52 between the flanges 59 and 61 are each flat and parallel to each other so that the mouthpiece will slide side wise in slot 36 but will not turn on its axise.

The upper surface 65 and the lower surface 66 of the bite block tubular portion 53 are also flat and parallel to each other to conform to the flat configuration of the upper and lower front teeth 34 and 35.

In operation the mouthpiece 52 is affixed in the slot 36 of faceplate 21 by flexing the material of the faceplate, in the area of the slot, around the front flange 59 until the faceplate is received in the gap 67 between flange 59 and flange 61. With the bit block portion 53 of the mouthpiece inserted in the patient's mouth, the ears of the faceplate are then bent to conform to the shape of the patient's face and the faceplate tied around the patient's head by the strands 31. The mountpiece may start in the central aperture 47 and the endotracheal tube 56 slid into the bore 57 and down into the trachea. A cuff not shown but well known, may then be inflated by the conduit 68 extending along a shallow groove 69 in the wall of the axial bore 57 in a well known manner. The endotracheal tube 56 is usually taped to the guide portion 54 of the mouthpiece to slide with the mouthpiece into side aperture 48 or 49 when the attendant or physician feels that the patient's mouth and teeth need relief. The other unused apertures permit insertion of other tubes into the mouth for any desired purpose.

I claim:

1. An endotracheal tube stabilizer comprising:

a faceplate of soft, flexible plastic material, said plate being of predetermined width at least equal to the width of the mouth of a patient and of predetermined height to abut and cover the area above and below said mouth;

said faceplate having a central wide slot therethrough substantially coextensive in width with the width of said mouth;

strand means on said faceplate, adapted to extend around the back of the head of a patient to firmly affix said faceplate over said mouth without the use of adhesive tape, a tubular mouthpiece mounted in said slot for sidewise sliding movement from one side thereof to the other, said mouthpiece having an axial bore, extending generally normal to said faceplate, for, receiving an endotracheal tube and having a tubular portion projecting into the mouth to form a bite block, and means for retaining said mouthpiece in said slot.

2. A stabilizer as specified in claim 1 wherein said mouthpiece includes a pair of integral spaced apart annular flanges, one in front and the other in rear of said faceplate, said flanges comprising said means for retaining said mouthpiece in said slot.

3. A stabilizer as specified in claim 2 wherein said faceplate includes upper and lower edges of said slot which are in substantial parallelism and said mouthpiece includes upper and lower flat surfaces, in the space between said flanges, which are parallel whereby said mouthpiece can be slid sidewise in said slot but cannot turn on its axis because of said flats.

4. A stabilizer as specified in claim 1 wherein said faceplate includes upper and lower edges of said slot which are in substantial parallelism, said edges having opposed pairs of spaced apart servations forming bendable barriers to the sliding of said mouthpiece dividing said slot into a left, side centre and right side aperture for receiving said mouth piece.

5. A stabilizer as specified in claim 1 wherein said mouthpiece includes a groove, extending axially along said bore, for receiving the inflation conduit of an inflatable cuff.

6. A stabilizer as specified in claim 1 wherein said mouthpiece includes an integral hollow cylindrical, flared tubular portion projecting away from the mouth of a patient to form a guide for receiving an endotracheal tube, and to which said endotracheal tube may be taped.

7. A stabilizer as specified in claim 2 wherein the said outer flange is of circular, flat disc configuration and the said inner flange is of generally square outline but curved configuration to conform to the curve of the teeth of a patient.

8. A stabilizer as specified in claim 1 wherein the tubular portion of said mouthpiece forming said bite block flat in the upper and lower quadrants thereof to conform to the configuration of a patient's upper and lower teeth.

9. An endotracheal tube stabilizer comprising:

a faceplate of flexible material engageable over the mouth of a patient and having a wide slot therein substantially coextensive in width with said mouth, and a mouthpiece supported for selective movement along said slot, said mouthpiece comprising a tubular member having an axial bore through which an endotracheal tube may be passed, a pair of annular flanges, one in front of, and one in rear of, said faceplate for retaining said mouthpiece in said slot, an inner projecting portion forming a bite block and an outer projecting portion forming a flared guide for said endotracheal tube:

10. An endotracheal tube stabilizer as specified in claim 9 wherein:

said faceplate includes integral flexible groups projecting into said slot at spaced distances therealong, to divide said slot into a left side, central and right side aperture each to frictionally retain said mouthpiece when slid along said slot from one position to another position.

11. An endotracheal tube stabilizer comprising:

a faceplate of soft flexible plastic material having strap means for securing the same around the back of the head of a patient said faceplate having a wide central slot substantially coextensive in width with the width of a patient's mouth and having upper and lower substantially parallel edges with a plurality of pairs of opposed integral prongs, or serrations, dividing said slot into a left side, a central, and a right side aperture, a tubular moiuthpiece supported for sidewise sliding movement in said slot for selective positioning successively in one of said apertures, said tubular mouthpiece having an axial bore, extending normal to said faceplate, for slidably receiving an endotracheal tube, and said tubular mouthpiece having flange means for retaining the same in said slot while permitting sidewise movement thereof whereby said mouthpiece may be periodically moved from one aperture to another, by flexing said prongs, to avoid damage from continuous pressure of the mouthpiece on the same spot in the mouth.

* * * * *